(12) United States Patent
Reese

(10) Patent No.: US 10,358,404 B2
(45) Date of Patent: *Jul. 23, 2019

(54) PROCESS FOR THE PRODUCTION OF LOW MOLECULAR WEIGHT IMPACT POLYETHERS

(75) Inventor: Jack R. Reese, Hurricane, WV (US)

(73) Assignee: Covestro LLC, Pittsburgh, PA (US)

( * ) Notice: Subject to any disclaimer, the term of this patent is extended or adjusted under 35 U.S.C. 154(b) by 1674 days.

This patent is subject to a terminal disclaimer.

(21) Appl. No.: 13/528,909

(22) Filed: Jun. 21, 2012

(65) Prior Publication Data

US 2013/0345476 A1    Dec. 26, 2013

(51) Int. Cl.
| | | |
|---|---|---|
| C07C 41/03 | (2006.01) | |
| C08G 65/26 | (2006.01) | |
| C08G 65/30 | (2006.01) | |

(52) U.S. Cl.
CPC .......... *C07C 41/03* (2013.01); *C08G 65/2609* (2013.01); *C08G 65/2663* (2013.01); *C08G 65/2696* (2013.01); *C08G 65/30* (2013.01)

(58) Field of Classification Search
CPC .................................................... C07C 41/03
See application file for complete search history.

(56) References Cited

U.S. PATENT DOCUMENTS

| | | | |
|---|---|---|---|
| 5,689,012 A | 11/1997 | Pazos et al. | |
| 5,723,094 A * | 3/1998 | Sunavala | B01J 4/001 422/607 |
| 5,777,177 A | 7/1998 | Pazos | |
| 5,919,988 A | 7/1999 | Pazos et al. | |
| 6,077,978 A | 6/2000 | McDaniel et al. | |
| 6,359,101 B1 | 3/2002 | O'Connor et al. | |
| 7,919,575 B2 | 4/2011 | Browne | |
| 2008/0021191 A1 | 1/2008 | Reese et al. | |
| 2012/0283483 A1* | 11/2012 | Weston | C08G 65/2609 568/624 |

FOREIGN PATENT DOCUMENTS

| | | |
|---|---|---|
| EP | 0868468 B1 | 7/2005 |
| WO | 9723544 | 7/1997 |
| WO | 2004111107 A1 | 12/2004 |
| WO | WO-2011/136376 * | 11/2011 |

OTHER PUBLICATIONS

Machine translation for WO 2011/136,376.*

* cited by examiner

*Primary Examiner* — Ana Z Muresan
(74) *Attorney, Agent, or Firm* — Richard P. Bender; N. Denise Brown

(57) ABSTRACT

This invention relates to an improved continuous process for the production of low molecular weight polyoxyalkylene polyether polyols. These polyoxyalkylene polyether polyols have a hydroxyl content of from about 3.4 to about 12.1% by weight, and may also be characterized as having an OH number of from about 112 to about 400. The process comprises establishing oxyalkylation conditions in a continuous reactor in the presence of a DMC catalyst; continuously introducing alkylene oxide and a low molecular weight starter into the continuous reactor; recovering a partially oxyalkylated polyether polyol from the reactor; and allowing the recovered partially oxyalkylated polyether polyol to further reactor until the unreacted alkylene oxide content of the mixture is reduced to 0.001% or less by weight.

26 Claims, No Drawings

PROCESS FOR THE PRODUCTION OF LOW MOLECULAR WEIGHT IMPACT POLYETHERS

BACKGROUND OF THE INVENTION

This invention relates to an improved process for the production of low molecular weight polyether polyols. The continuous process polymerizes an alkylene oxide with a starter compound in the presence of a double metal cyanide catalyst.

The preparation of polyoxyalkylene polyols by double metal cyanide (DMC) catalysts is known and described in, for example U.S. Pat. Nos. 5,689,012, 5,777,177 and 5,919,988. The polyoxyalkylene polyols produced by DMC catalysis are characterized by low unsaturation and low polydispersity (i.e. a narrow molecular weight range). One advantage of double metal cyanide catalysts is that they do not promote the rearrangement of propylene oxide into propenyl alcohol which acts as a monofunctional initiator in propylene oxide polymerization. The presence of propenyl alcohol promotes the formation of monoalcohols which are an impurity in the process.

Another advantage of double metal cyanide catalysts includes the ability to leave the catalyst residue in the product. This results in lower production cost since the catalyst residues do not have to be stripped or otherwise removed from the polyoxyalkylene polyol prior to use.

While double metal cyanide catalysts provide numerous advantages in preparing polyoxyalkylene polyols, there are, unfortunately, some disadvantages to this type of catalysis. See U.S. Pat. Nos. 5,777,177, 6,077,978 and 7,919,575. These disadvantages include the tendency of the catalyst to deactivate in the presence of high concentrations of hydroxyl groups, the inability to polymerize in the presence of low molecular weight initiators such as glycerin, and the fact that, in addition to the desired product, DMC catalysts produce a small quantity of a very high molecular weight (i.e. at least 100,000 MW and higher) polymer. This high molecular weight polymer is commonly referred to high molecular weight tail. High molecular weight tail causes difficulties with the foaming process when reacting a polyol with a polyisocyanate to produce a polyurethane foam.

There have been numerous efforts over the last few years to improve and extend double metal cyanide catalysis to enable effective oxyalkylation of low molecular weight starters such as glycerin, and to produce low molecular weight polyoxyalkylene polyols. In particular, U.S. Pat. No. 6,077,978 describes direct polyoxyalkylation of glycerin with a DMC catalyst in which catalyst deactivation is decreased by i) acidifying the acid sensitive low molecular weight starter prior to introducing the acid sensitive starter into the reactor; ii) treating the acid sensitive low molecular weight starter with an effective amount of a base-reactive or base-absorptive substance other than an acid prior to introducing the low molecular weight starter into the reactor; and iii) adding an effective amount of an acid to prevent catalyst deactivation to the reactor in which the acid is not contained in a feed stream containing acid sensitive low molecular weight starter.

U.S. Pat. No. 7,919,575 describes a polyoxyalkylation process using a double metal cyanide (DMC) catalyst in which the low molecular weight starter is acidified with at least one of an inorganic protic mineral acid and an organic acid, wherein the acid is present in an amount of greater than that required to neutralize the basicity of the low molecular weight starter. Typically, the acid is present in an amount of greater than 100 ppm, based on the weight of the starter. This process permits the use of a smaller quantity of catalyst, and enables low molecular weight starters to be used in the process without catalyst deactivation.

Another process for producing polyethers using DMC catalysts is described in U.S. Published Patent Application 2008/0021191. This process uses 5 to 1000 ppm of a double metal cyanide catalyst in the oxyalkylation reaction, and requires that the low molecular weight starter has a number average molecular weight of less than about 300 Daltons, contains from about 200 to about 5000 ppm of water, and is acidified with from about 10 to about 2000 ppm of at least one of an inorganic protic mineral acid and an organic acid. The addition of the acid to the low molecular weight starter which contains a relatively high water content minimizes and/or prevents catalyst deactivation due to the water.

U.S. Pat. No. 6,359,101 also describes a process for preparing polyether polyols from double metal cyanide catalysts. This process comprises polymerizing an epoxide in the presence of DMC catalyst and a continuously added first starter, wherein the epoxide and first starter are continuously added to the reactor during step (a) to produce an intermediate, and (b) reacting the polyol intermediate with additional epoxide, and optionally, additional DMC catalyst and a second starter to product a polyether polyol. Suitable starters include 1,6-hexanediol, cyclohexane dimethanol, bishydroxyethyl hydroquinonone, bishydroxyethyl resorcinol, etc. In addition, the mole ratio of epoxide to total first starter is at least about 3:1, and the first starter added in step (a) has an impurity level (of total amount of water, propylene glycol and neutralized base residues) of less than about 100 ppm by weight.

The present invention allows the preparation of low molecular weight polyoxyalkylene polyether polyols from a continuous process in which a low molecular weight starter is alkoxylated in the presence of a double metal cyanide catalyst. It has been found that carefully maintaining the oxyalkylation reaction at a sufficiently high temperature prevents catalyst deactivation, even in the presence of high levels of low molecular weight starters. Advantages of the present invention include efficient, sustainable production of low molecular weight products useful in polyurethane applications. The present invention also provides an efficient and sustainable means to produce low molecular weight polyether products that are useful as starters for higher molecular weight polyether products. The present invention allows the production of low molecular weight polyethers at optimized DMC catalyst concentrations by utilizing the higher reaction temperature. One skilled in the art will recognize that a continuous process is more efficient than a batch or semi-batch process typically used to make low molecular weight polyether products and/or polyether starters.

SUMMARY OF THE INVENTION

This invention relates to a continuous process for the production of polyoxyalkylene polyether polyols. These polyoxyalkylene polyether polyols have a hydroxyl content of from about 3.4 to about 12.1%, by weight. This continuous process comprises:

establishing oxyalkylation conditions in a continuous oxyalkylation reactor in the presence of a double metal cyanide (DMC) catalyst;

continuously introducing alkylene oxide and a low molecular weight starter into the continuous oxyalkylation reactor, wherein the starter has a number average molecular weight of from 50 to 250, preferably from 50 to 230, more preferably from 50 to 200 and most preferably from 50 to 100;

recovering a partially oxyalkylated polyether polyol from the continuous oxyalkylation reactor;

wherein (i) said oxyalkylation in the continuous oxyalkylation reactor occurs at a sufficiently high temperature (preferably at least at 135° C., and more preferably at least 140° C.) to prevent deactivation of the DMC catalyst; (ii) the concentration of unreacted alkylene oxide in the contents of the continuous reactor is maintained at a level of from 1 to 3% (preferably 1 to 2%) by weight; and (iii) the hydroxyl content of the reactor contents is maintained at 3.4 to 12.1% by weight;

and allowing further reaction of the partially oxyalkylated polyether polyol which is recovered from the continuous oxyalkylation reactor to occur until the unreacted alkylene oxide content of the mixture is reduced to 0.001% or less (preferably 0.0005% or less) by weight.

A continuous process for the production of a polyoxyalkylene polyether polyol having a hydroxyl content of from about 3.4 to about 12.1% by weight, which comprises:

establishing oxyalkylation conditions in a continuous oxyalkylation reactor in the presence of a double metal cyanide catalyst;

continuously introducing alkylene oxide and a low molecular weight starter into said continuous oxyalkylation reactor, wherein said starter has at least two hydroxyl groups per molecule and an equivalent weight of up to 115;

recovering a partially oxyalkylated polyether polyol from the continuous oxyalkylation reactor;

wherein (i) said oxyalkylation in the continuous oxyalkylation reactor occurs at a sufficiently high temperature (preferably at least at 135° C., and more preferably at least 140° C.) to prevent deactivation of the DMC catalyst; (ii) the concentration of unreacted alkylene oxide in the contents of the continuous reactor is maintained at a level of from 1 to 3% by weight; and (iii) the hydroxyl content of the reactor contents is maintained at 3.4 to 12.1% by weight;

and allowing further reaction of the partially oxyalkylated polyether polyol which is recovered from the continuous oxyalkylation reactor to occur until the unreacted alkylene oxide content of the mixture is reduced to 0.001% or less by weight.

In the above embodiment, it is preferred that the build ratio in the continuous oxyalkylation reactor is from 4.6 to 16.2 and the overall build ratio is from 4.6 to 16.2, and that the temperature of the reaction mixture in the further reaction step increases by up to 35° C. as a result of the exothermic polymerization reaction.

The present invention also relates to a continuous process for the production of a polyoxyalkylene polyether polyol having a hydroxyl content of from about 3.4 to about 12.1% by weight. This process comprises:

continuously polymerizing at least one alkylene oxide in the presence of a double metal cyanide (DMC) catalyst in a continuous reactor;

feeding a low molecular weight starter that has at least two hydroxyl groups per molecule and an equivalent weight of up to 115 and at least one alkylene oxide to the continuous reactor containing alkylene oxide and a double metal cyanide catalyst;

recovering a partially oxyalkylated polyol mixture from the continuous reactor;

wherein (i) the continuous reactor is maintained at a polymerization temperature that is greater than or equal to 135° C. (preferably that is greater than or equal to 140° C.), (ii) the concentration of unreacted alkylene oxide in the contents of the continuous reactor is maintained at a level of from 1 to 3% (preferably 1 to 2%) by weight, and (iii) the hydroxyl content of the reactor contents is maintained at 3.4 to 12.1% by weight;

and subsequently, the partially oxyalkylated polyol mixture which is withdrawn from the continuous reactor is permitted to further react until the unreacted alkylene oxide content of the mixture is reduced to 0.001% or less (preferably 0.0005% or less) by weight.

In the above embodiment, it is preferred that the build ratio in the continuous oxyalkylation reactor is from 4.6 to 16.2 and the overall build ratio is from 4.6 to 16.2, and that the temperature of the reaction mixture in the further reaction step increases by up to 35° C. as a result of the exothermic polymerization reaction.

Another aspect of the present invention relates to a process for continuously polymerizing an alkylene oxide in the presence of a double metal cyanide (DMC) polymerization catalyst to form a polyether polyol having a hydroxyl content of from about 3.4 to about 12.1% by weight, wherein in a first step a), an initiator compound that has at least two hydroxyl groups per molecule and an equivalent weight of up to 115 and at least one alkylene oxide are fed to a continuous reactor containing a double metal cyanide catalyst, and a partially polymerized mixture is withdrawn from the continuous reactor;

wherein (i) the continuous reactor is maintained at a polymerization temperature that is greater than or equal to 135° C. (preferably that is greater than or equal to 140° C.), (ii) the concentration of unreacted alkylene oxide in the contents of the continuous reactor is maintained at a level of from 1 to 3% (preferably 1 to 2%) by weight, and (iii) the hydroxyl content of the reactor contents is maintained at 3.4 to 12.1% by weight, and in a subsequent step b), the partially polymerized mixture which is withdrawn from the reactor in step a) is permitted to further react until the unreacted alkylene oxide content of the mixture is reduced to 0.001% or less (preferably 0.0005% or less) by weight.

In the above embodiment, it is preferred that the build ratio in step a) is from 4.6 to 16.2 and the overall build ratio of from 4.6 to 16.2, and that the temperature of the reaction mixture in step b) increases by up to 35° C. as a result of the exothermic polymerization reaction.

The present invention also relates to a continuous process for the production of a polyoxyalkylene polyether polyol having an OH number of from 112 to 400 (preferably 200 to 375). This process comprises:

(1) establishing oxyalkylation conditions in a continuous oxyalkylation reactor in the presence of a double metal cyanide (DMC) catalyst;
(2) continuously introducing alkylene oxide and a low molecular weight starter into said reactor, wherein the low molecular weight starter has a number average molecular weight of from 50 to 250, preferably from 50 to 230, more preferably from 50 to 200 and most preferably from 50 to 100;
and
(3) recovering a partially oxyalkylated polyether polyol from the continuous oxyalkylation reactor;
wherein (i) the oxyalkylation in the continuous reactor occurs at a sufficiently high temperature to prevent deactivation (preferably at least 135° C., and more preferably at least 140° C.) of the DMC catalyst; and (4) further reacting the partially oxyalkylated polyether polyol which is recovered from the continuous oxyalkylation reactor, thereby forming the polyoxyalkylene polyether polyol having an OH number of from 112 to 400 (preferably 200 to 375).

In a preferred embodiment of this continuous process, the build ratio in the continuous oxyalkylation reactor is from 4.6 to 16.2 and the overall build ratio is from 4.6 to 16.2, and the temperature of the reaction mixture in step (4) the further reaction step, increases by up to 35° C. as a result of the exothermic polymerization reaction.

A particularly preferred embodiment of the present invention is directed to a process for the production of a polyoxyalkylene polyether polyol that comprises continuously polymerizing an alkylene oxide in the presence of a double metal cyanide (DMC) polymerization catalyst to form a polyether polyol having a hydroxyl content of from about 3.4 to about 9.1% by weight, wherein in a first step a), an initiator compound that has at least two hydroxyl groups per molecule and an equivalent weight of up to 115 and at least one alkylene oxide are fed to a continuous reactor containing a double metal cyanide catalyst, and a partially polymerized mixture is withdrawn from the continuous reactor;

wherein (I) the continuous reactor is maintained at a polymerization temperature that is greater than or equal to 135° C. (preferably that is greater than or equal to 140° C.), (ii) the concentration of unreacted alkylene oxide in the contents of the continuous reactor is maintained at a level of from 1 to 3% (preferably 1 to 2%) by weight, and (iii) the hydroxyl content of the reactor contents is maintained at 3.4 to 9.1% by weight, and in a subsequent step b), the partially polymerized mixture which is withdrawn from the reactor in step a) is permitted to further react until the unreacted alkylene oxide content of the mixture is reduced to 0.001% or less (preferably 0.0005% or less) by weight;

wherein the build ratio in step a) is from 6.1 to 16.2 and the overall build ratio of from 6.1 to 16.2, and wherein the temperature of the reaction mixture in step b) increases by up to about 24° C. as a result of the exothermic polymerization reaction.

DETAILED DESCRIPTION OF THE INVENTION

The present invention will now be described for purposes of illustration. Except in the operating examples, or where otherwise indicated, all numbers expressing quantities, percentages, OH numbers, functionalities, and so forth in the specification are to be understood as being modified by the term "about'.

As used herein, all molecular weights are number average molecular weights unless otherwise specified.

The continuous process described herein is suitable for the production of polyoxyalkylene polyether polyols. These polyoxyalkylene polyether polyols are characterized as having a hydroxyl content of from about 3.4 to about 12.1% by weight, based on 100% by weight of the polyoxyalkylene polyether polyols. The polyoxaylkylene polyether polyols produced by this process may also be described as typically having an OH number of from at least about 112, and preferably from at least about 200. These polyoxyalkylene polyether polyols also typically have an OH number of less than or equal to about 400, and preferably of less than or equal to about 375. The polyoxyalkylene polyether polyols may also have an OH number ranging between any combination of these upper and lower values, inclusive, such as, for example from at least about 112 to less than or equal to about 400, and preferably from at least about 200 to less than or equal to about 375.

As is known by one skilled in the art, OH numbers of from about 112 to about 400 correspond to equivalent weights of about 500 to about 140, respectively; and OH numbers of from about 200 to about 375 correspond to equivalent weights of from about 280 to about 150, respectively.

In addition, the conversion of OH number to hydroxyl content and from hydroxyl content to OH number is easily calculated and readily determined by one of ordinary skill in the art. A polyoxyalkylated polyether polyol having an OH number of about 112 will have a hydroxyl content of about 3.4% by weight, and a polyoxyalkylated polyether polyol having an OH number of about 400 will have a hydroxyl content of about 12.1% by weight.

The polyoxyalkylene polyether polyols prepared by the presently claimed process typically have a hydroxyl content of at least about 3.4%, preferably at least about 6%, and more preferably at least about 7% by weight. These polyoxyalkylene polyether polyols also typically have a hydroxyl content of less than or equal to 12.1%, preferably less than or equal to 11.4%, more preferably less than or equal to 10.6% and most preferably less than or equal to 9.1% by weight. The polyoxyalkylene polyether polyols may have a hydroxyl content ranging between any combination of these upper and lower values, inclusive, e.g., from 3.4% to 12.1%, preferably from 6% to 11.4%, more preferably from 7% to 10.6% and most preferably from 7% to 9.1% by weight, based on 100% by weight of the polyoxyalkylene polyols.

Suitable double metal cyanide (DMC) catalysts to be used in the process of the present invention include, for example, any known DMC catalyst. These include both the crystalline and the substantially non-crystalline (i.e. substantially amorphous) DMC catalysts. Crystalline DMC catalysts are known and described in, for example, U.S. Pat. No. 5,158, 922, 4,477,589, 3,427,334, 3,941,849 and 5,470,813, the disclosures of which are hereby incorporated by reference. Double metal cyanide (DMC) catalysts which exhibit a substantially non-crystalline character (i.e. are substantially amorphous) are known and described in, for example, U.S. Pat. Nos. 5,482,908 and 5,783,513, the disclosures of which are hereby incorporated by reference.

The catalysts disclosed in U.S. Pat. Nos. 5,482,908 and 5,783,513 differ from other DMC catalysts because these catalysts exhibit a substantially non-crystalline morphology. In addition, these catalysts are based on a combination of ligands, such as t-butyl alcohol and a polydentate ligand (polypropylene oxide polyol). Zinc hexacyanocobaltates are preferred DMC catalysts. Preferred DMC catalysts are the substantially amorphous catalysts.

The DMC catalyst concentration in the inventive process is chosen to ensure a good control of the polyoxyalkylation reaction under the given reaction conditions. The catalyst concentration is preferably in the range from 15 ppm to 200 ppm, more preferably in the range from 20 ppm to 150 ppm, most preferably in the range from 30 to 120 ppm, based on the weight of the polyether polyol produced. The crystalline and the substantially non-crystalline DMC catalysts may be present in an amount ranging between any combination of these values, inclusive of the recited values.

Suitable low molecular weight starter compounds include compounds which have a functionality of at least about 2 up to about 8, and preferably from about 2 to about 6, and which have an equivalent weight of up to about 115, and preferably up to about 100. Suitable starter compounds include, but are not limited to, $C_3$-$C_5$ monols, ethylene glycol, propylene glycol, 1,3-propanediol, 1,4-butanediol, 1,2-butanediol, 1,3-butanediol, 2,3-butanediol, water, glycerin, sorbitol, etc. Mixtures of monomeric initiators or their oxyalkylated oligomers may also be utilized. Preferred starter compounds are propylene glycol and glycerin. Glycerin is the most preferred starter compound.

Starter compounds may also be referred to as initiators.

The suitable low molecular weight starter compounds may also be described as compounds having the above described functionality and a number average molecular weight of less than or equal to about 250, preferably less than or equal to about 230, more preferably less than or equal to about 200, and most preferably less than or equal to about 100. Typically, the starter compound has a number average molecular weight of at least about 50.

Alkylene oxides useful in the present invention include, but are not limited to, ethylene oxide, propylene oxide, 1,2- and 2,3-butylene oxide, isobutylene oxide, epichlorohydrin, cyclohexene oxide, and styrene oxide. Propylene oxide alone or mixtures of propylene oxide with ethylene oxide, preferably at a ratio of 85:15 and more preferably at a ratio of 90:10, are preferred for use in the present invention. Other alkylene oxides mixed with propylene oxide may also prove useful in the inventive processes. Propylene oxide alone is the most preferred alkylene oxide.

In the process of the invention, oxyalkylation conditions are established in the continuous reactor by charging a polyether polyol containing a double metal cyanide (DMC) catalyst to the continuous reactor, preferably a continuous stirred tank reactor. The polyether polyol should contain from about 30 to about 120 ppm of DMC catalyst. Once the polyether polyol containing DMC catalyst has been charged to the reactor, the reactor contents are slowly heated to a temperature of 135° C., and preferably at least 140° C. The reactor contents in the first step of the process may be heated to temperatures as high as 190° C. or higher, but preferably the temperature does not exceed 180° C., more preferably the temperature is 160° C. or less and most preferably the temperature is 150° C. or less. The reactor contents may be heated to a temperature ranging between any combination of these upper and lower values, inclusive. Once the reactor and contents are heated, an initial charge of an alkylene oxide, preferably propylene oxide, is charged to the reactor over a time period of 5 to 10 minutes. Within a short time period, i.e. from about 5 to about 10 minutes, the pressure in the reactor will drop, which indicates that the DMC catalyst has been activated.

Once the DMC catalyst is activated, a feed stream of at least one alkylene oxide (preferably propylene oxide) is started and continuously feed to the reactor. In addition, a separate feed stream of a low molecular weight starter having a molecular weight of from 50 to 250 (or one of the possible ranges described herein) is started and continuously feed to the reactor. The feed stream of the low molecular weight starter also typically contains DMC catalyst in an amount of from 130 to 2000 ppm, depending on the final product hydroxyl number and the final desired catalyst concentration. An alternative method for the catalyst addition is to have a $3^{rd}$ stream that contains a catalyst loading of 1 to 2 weight % in either the low molecular starter or a low molecular weight polyether. In this alternative method, the $2^{nd}$ stream contains low molecular weight starter and is free of DMC catalyst; and the $1^{st}$ steam comprises the alkylene oxide.

Oxyalkylation occurs in the reactor at a temperature that is sufficient to prevent deactivation of the DMC catalyst. Preferably, this temperature is at least 135° C., and more preferably at least 140° C. The maximum temperature in the reactor is about 190° C. or higher, but preferably the temperature does not exceed 180° C., more preferably the temperature is 160° C. or less and most preferably the temperature is 150° C. or less. Oxyalkylation in the reactor may occur at a temperature between any combination of these upper and lower values, inclusive. The oxyalkylation reaction continues for at 4 residence times or more, and preferably 6 residence times or more while maintaining a positive temperature differential between the reaction temperature and the temperature of the cooling/heating loop thus indicating an exothermic reaction that requires cooling. During the oxyalkyation, the concentration of unreacted alkylene oxide in the contents of the continuous reactor is maintained at a level of from 1 to 3%, preferably 1 to 2%, by weight, based on the total weight of the contents in the reactor, and the hydroxyl content of the reactor contents is maintained in the range of from 3.4 to 12.1% by weight (or any of the other suitable ranges for hydroxyl content), based on 100% by weight of the reactor contents.

Recovery of the partially oxyalkylated polyether polyol from the continuous oxyalkylation reactor is preferably continuous but may be intermittent in some embodiments. The temperature at which the partially oxyalkylated polyether polyol further reacts can increase during this step due to the exothermic reaction of the residual alkylene oxide onto the end of the polymer chains. Minimal or no external cooling is typically applied at this point in the process. In addition, it is not typically necessary to heat this portion of the process due to the exothermic nature of the polymerization reaction that occurs here. In general, the temperature of the reaction mixture entering this step of the process is at least about 140° C. or greater, and preferably at least about 160° C. or greater. The temperature of the reaction mixture entering this step is also typically less than or equal to about 220° C., preferably less than or equal to about 200° C., and more preferably less than or equal to about 185° C. The temperature of the reaction mixture may range between any combination of these lower and upper values, inclusive, e.g. from at least about 140° C. to less than or equal to about 220° C., preferably from at least about 140° C. to less than or equal to about 200° C., and more preferably from at least about 160° C. to less than or equal to about 185° C.

In addition, the reaction mixture in this step or portion of the process may increase in temperature by up to 35° C. as a result of the exothermic polymerization. Generally, however, the temperature increase of this reaction mixture is more typically from about 10° C. to about 25° C. In a preferred embodiment, the temperature increase of the reaction mixture increases up to about 24° C. due to the exothermic polymerization.

The partially completed (i.e. oxyalkylated) polyether polyol is continuously removed from the full liquid reactor through a back pressure regulator. The partially oxyalkylated polyether polyol is allowed to further react until the unreacted alkylene oxide content of the reaction mixture is reduced to 0.001% or less, preferably 0.0005% or less, by weight. The final product typically contains small amounts of catalyst residues, i.e. less than or equal to about 100 ppm, more preferably less than or equal to 50 ppm; small quantities of the initiator compound or low molecular weight alkoxylates thereof; and small amounts of other organic impurities and water. As is known in the production of polyoxyalkylated polyether polyols, volatile compounds can be flashed or stripped from the polyols, and catalyst residues may remain in the product or may be removed. Moisture can be removed by stripping the polyols.

It is preferred that the partially oxyalkylated polyether polyols further reacts in a pipe reactor. This typically occurs by passing the partially oxyalkylated polyether polyol through a pipe reactor that is steam heated to maintain a high temperature of about 145° C. for reaction of the remaining alkylene oxide. It is preferred that the further reaction of the partially oxyalkylated polyether polyol occurs isothermally.

The minimum build ratios for the continuous oxyalkylation reactor are typically at least about 4.6, preferably at least about 4.9, more preferably at least about 5.2 and most preferably at least about 6.1. The maximum build ratios for the continuous oxyalkylation reactor are typically less than or equal to about 16.2, preferably less than or equal to about 9.1, and more preferably less than or equal to about 7.9. The build ratios for the continuous oxyalkylation reactor may range from any combination of these upper and lower values, inclusive, such as, for example, from at least about 4.6 to less than or equal to about 16.2, preferably from at least about 4.9 to less than or equal to about 9.1, and more preferably from at least about 5.2 to less than or equal to about 7.9. These same build ratios are also suitable for the overall process. It is particularly preferred to use a build ratio of from 5.2 to 7.9 when glycerin is the low molecular weight starter. Another preferred build ratio for the invention ranges from at least about 6.1 to about less than or equal to about 16.2.

In accordance with the present invention, it is preferred that the low molecular weight starter is acidified with a small amount of a suitable acid as described in, for example, U.S. Pat. No. 6,077,978 and U.S. Pat. No. 7,919,575, the disclosures of which are herein incorporated by reference. The acid may be any inorganic protic mineral acid or organic acid which is known to suitable as described in the art. Typically, the amount of acid to be added to the low molecular weight starter ranges from 30 to 200 ppm, based on the weight of the low molecular weight starter. Preferably, the starter contains from 30 to 100 ppm of acid. Phosphoric acid is the preferred acid.

When using a $3^{rd}$ stream containing an acidified low molecular weight starter or polyol as the catalyst carrier (see the alternate embodiment described above) the acid level in the mixture of carrier and catalyst is less than 1500 ppm. Preferably the mixture of low molecular weight starter or polyol catalyst carrier and the catalyst contains less than 1250 ppm of acid.

The term "partially" with regard to the oxyalkylated polyether polyols formed in the processes of the present invention may be understood to mean that the oxyalkylation of the starter to form the polyether polyol is substantially completed. In other words, after the oxyalkylated polyether polyol is recovered or removed from the continuous oxyalkylation reactor, a minor amount of reaction occurs outside of the reactor. More specifically, at the point the oxyalkylated polyether polyol is recovered from the continuous oxyalkylation reactor, the reaction is preferably at least 98% complete, more preferably at least 98.5% complete, and most preferably at least 99% complete.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all parts and percentages are parts by weight and percentages by weight, respectively.

EXAMPLES

Example 1 (Comparative)

A 238 hydroxyl number glycerine-based all-PO polyether (about 3000 grams) containing 60 ppm of DMC catalyst which was prepared according to the procedure in U.S. Pat. No. 5,482,908 was charged to a 1 gallon stainless steel reactor equipped with a mechanical agitator and slowly heated. During the heat-up, continuous vacuum was pulled on the headspace and nitrogen was introduced to the liquid phase via a dip tube. Once the reactor temperature reached 130° C., the vacuum and nitrogen continued for an additional ten minutes, the nitrogen was then stopped and the reactor was blocked in at a pressure of 1.5 psia. An initial charge of PO was charged to the reactor over several minutes. After 10 minutes, the pressure in the reactor decreased indicating that the DMC catalyst was active. The PO feed was restarted and set at a rate of 19.83 g/min (equivalent to a 2.5 hour residence time). After establishing the oxide feed, a feed containing glycerin with 576 ppm of DMC catalyst and 75 ppm phosphoric acid was started at a rate of 3.89 g/min. The DMC catalyst was added to the glycerine by constant agitation of the glycerin/DMC catalyst feed vessel. The glycerin/catalyst feed line may have constant recirculation between the reactor feed point and the glycerin/DMC catalyst feed vessel to eliminate settling of the catalyst in the feed line, although constant recirculation was not used in the present examples unless otherwise noted. The DMC concentration in the glycerin is sufficient to provide 95 ppm of DMC catalyst in the final product. When the pressure in the reactor reached 40 psia, a valve at the top of the reactor was opened to a back pressure regulator and the liquid contents of the full continuously stirred tank reactor were allowed to flow out of the reactor. The polyether passed through a steam heated section of pipe before being collected in a heated and stirred jacketed vessel. After approximately 2 hours of oxide feed to the stirred jacketed vessel, the reactor cooling system switched to heating indicating a loss of reaction. After an additional 45 minutes of heating with no sign of reaction, the oxide feeds and glycerin/DMC feeds were stopped.

Example 2 (Invention)

Using a similar start-up procedure as set forth in Example 1, the reaction temperature was set at 140° C. prior to starting the PO and glycerin/DMC feeds. The PO was fed at a constant rate of 19.83 g/min (equivalent to a 2.5 hour residence time). The glycerin/DMC feed contained 576 ppm of DMC catalyst and 75 ppm phosphoric acid, and was fed at a constant rate of 3.89 g/min. When the pressure in the reactor reached 40 psia, a valve at the top of the reactor was opened to a back pressure regulator and the liquid contents of the full continuously stirred tank reactor were allowed to flow out of the reactor. The polyether passed through a steam heated section of pipe before being collected in a heated and stirred jacketed vessel. The run continued for approximately 18 hours (7 residence times) at which point the feeds were stopped. The collected product had a measured hydroxyl number of 304 mg KOH/g and a viscosity of 301 cSt at 25° C.

Example 3 (Comparative)

Using the final reactor contents as described in Example 2 as the starter and a similar start-up procedure as set forth in Example 1, the reaction temperature was decreased to 130° C., the PO feed was re-started at 19.83 g/min and the glycerin/DMC feed containing 576 ppm of DMC catalyst and 75 ppm phosphoric acid was re-started at a rate of 3.89 g/min. After 60 minutes, the reactor cooling system switched to heating indicating a loss of reaction. After an additional 10 minutes of heating with no sign of reaction, the PO and glycerin/DMC catalyst feeds were stopped.

Example 4 (Inventive)

Using the final reactor contents as described in Example 3 and a similar start-up procedure as set forth in Example 1, the reaction temperature was increased to 140° C., the PO feed was re-started at 19.83 g/min and the glycerin/DMC feed containing 576 ppm DMC catalyst and 75 ppm phosphoric acid was re-started at a rate of 3.89 g/min. The reaction continued for 4 hours with a good heat of reaction at which point the feeds were stopped. This demonstrated that the reaction occurred at the reaction temperature of 140° C.

Examples 2 and 4 demonstrate that using a slightly higher reaction temperature than that which was used in Examples 1 and 3 will restart the reaction and provide a steady state process.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A continuous process for the production of a polyoxyalkylene polyether polyol having a hydroxyl content of from about 3.4 to about 12.1% by weight, which comprises:
   establishing oxyalkylation conditions in a continuous oxyalkylation reactor in the presence of a double metal cyanide catalyst;
   continuously introducing alkylene oxide and a low molecular weight starter into said continuous oxyalkylation reactor, wherein said starter has a number average molecular weight of from 50 to 250;
   continuously recovering a partially oxyalkylated polyether polyol from the continuous oxyalkylation reactor;
   wherein (i) said oxyalkylation in the continuous oxyalkylation reactor occurs at a sufficiently high temperature to prevent deactivation of the DMC catalyst; (ii) the concentration of unreacted alkylene oxide in the contents of the continuous reactor is maintained at a level of from 1 to 3% by weight; and (iii) the hydroxyl content of the reactor contents is maintained at 3.4 to 12.1% by weight; and
   allowing further reaction of the partially oxyalkylated polyether polyol which is recovered from the continuous oxyalkylation reactor to occur until the unreacted alkylene oxide content of the mixture is reduced to 0.001% or less by weight, wherein the further reaction of the partially oxyalkylated polyether polyol occurs isothermally.

2. The process of claim 1, wherein the resultant polyoxyalkylene polyether polyol has a hydroxyl number of from about 112 to about 400.

3. The process of claim 1 wherein the build ratio in said continuous oxyalkylation reactor is from 4.6 to 16.2.

4. The process of claim 1, wherein the overall build ratio is from 4.6 to 16.2.

5. The process of claim 1, wherein the alkylene oxide is propylene oxide or a mixture of propylene oxide and ethylene oxide that contains at least 85% by weight of propylene oxide.

6. The process of claim 1, wherein the hydroxyl content of the reactor contents is maintained at 6 to 11.4% by weight.

7. The process of claim 1, wherein the unreacted alkylene oxide in the contents of said continuous oxyalkylation reactor is maintained at a level of from 1 to 2% by weight.

8. The process of claim 1, wherein said low molecular weight starter comprises glycerine.

9. The process of claim 1, wherein said continuous oxyalkylation reactor is a continuously stirred tank reactor and said further reaction of the partially oxyalkylated polyether polyol is performed in a pipe reactor.

10. The process of claim 1, wherein the concentration of the double metal cyanide catalyst in said continuous oxyalkylation reactor is from 30 to 120 ppm, based on the weight of the product.

11. The process of claim 1, wherein the temperature in said continuous oxyalkylation reactor is at least 135° C.

12. The process of claim 1, wherein the temperature in said continuous oxyalkylation reactor is from at least 135° C. to 160° C.

13. The process of claim 1, wherein the double metal cyanide catalyst is a zinc hexacyanocobaltate catalyst complex.

14. The process of claim 1, wherein the resultant polyoxyalkylene polyether polyol has a hydroxyl content of from 7 to 10.6% by weight.

15. The process of claim 1, wherein said low molecular weight starter comprises glycerine and the overall build ratio is from 5.2 to 7.9.

16. The process of claim 1, wherein the partially oxyalkylated polyether polyol which is recovered from the continuous oxyalkylation reactor passes through a pipe reactor that is steam heated to maintain a high temperature of about 145° C. for reaction of the remaining oxide until the unreacted alkylene oxide content of the mixture is reduced to 0.0005% or less by weight.

17. A continuous process for the production of a polyoxyalkylene polyether polyol having a hydroxyl content of from about 3.4 to about 12.1% by weight, which comprises:
   establishing oxyalkylation conditions in a continuous oxyalkylation reactor in the presence of a double metal cyanide catalyst;
   continuously introducing alkylene oxide and a low molecular weight starter into said continuous oxyalkylation reactor, wherein said starter has at least two hydroxyl groups per molecule and an equivalent weight of up to 115;
   continuously recovering a partially oxyalkylated polyether polyol from the continuous oxyalkylation reactor;
   wherein (i) said oxyalkylation in the continuous oxyalkylation reactor occurs at a sufficiently high temperature to prevent deactivation of the DMC catalyst; (ii) the concentration of unreacted alkylene oxide in the contents of the continuous reactor is maintained at a level of from 1 to 3% by weight; and (iii) the hydroxyl content of the reactor contents is maintained at 3.4 to 12.1% by weight;

and allowing further reaction of the partially oxyalkylated polyether polyol which is recovered from the continuous oxyalkylation reactor to occur until the unreacted alkylene oxide content of the mixture is reduced to 0.001% or less by weight;

wherein the build ratio in the continuous oxyalkylation reactor is from 4.6 to 16.2 and the overall build ratio is from 4.6 to 16.2, wherein the temperature of the reaction mixture in said further reaction step increases by up to 35° C. as a result of the exothermic polymerization reaction, and wherein the further reaction of the partially oxyalkylated polyether polyol occurs isothermally.

18. A continuous process for the production of a polyether polyol having a hydroxyl content of from about 3.4 to about 12.1% by weight, which comprises:

continuously polymerizing at least one alkylene oxide in the presence of a double metal cyanide catalyst in a continuous reactor;

feeding a low molecular weight starter that has at least two hydroxyl groups per molecule and an equivalent weight of up to 115, and at least one alkylene oxide to said continuous reactor containing alkylene oxide and a double metal cyanide catalyst;

continuously recovering a partially oxyalkylated polyol mixture from the continuous reactor;

wherein (i) the continuous reactor is maintained at a polymerization temperature of greater than or equal to 135° C., (ii) the concentration of unreacted alkylene oxide in the contents of the continuous reactor is maintained at a level of from 1 to 3% by weight, and (iii) the hydroxyl content of the reactor contents is maintained at 3.4 to 12.1% by weight;

and subsequently, the partially oxyalkylated polyol mixture which is withdrawn from the continuous reactor is permitted to further react until the unreacted alkylene oxide content of the mixture is reduced to 0.001% or less by weight;

wherein the build ratio in the continuous oxyalkylation reactor is from 4.6 to 16.2 and the overall build ratio is from 4.6 to 16.2, wherein the temperature of the reaction mixture in said further reaction step increases by up to 35° C. as a result of the exothermic polymerization reaction, and wherein the further reaction of the partially oxyalkylated polyol mixture occurs isothermally.

19. The process of claim 18, wherein the resultant polyether polyol has an OH number of from about 112 to about 400.

20. A process for continuously polymerizing an alkylene oxide in the presence of a double metal cyanide polymerization catalyst to form a polyether polyol having a hydroxyl content of from about 3.4 to about 12.1% by weight, wherein:

in a first step a), an initiator compound that has at least two hydroxyl groups per molecule and an equivalent weight of up to 115, and at least one alkylene oxide are fed to a continuous reactor containing a double metal cyanide catalyst, and a partially polymerized mixture is withdrawn from the continuous reactor;

wherein (i) the continuous reactor is maintained at a polymerization temperature of greater than or equal to 135° C., (ii) the concentration of unreacted alkylene oxide in the contents of the continuous reactor is maintained at a level of from 1 to 3% by weight, and (iii) the hydroxyl content of the reactor contents is maintained at 3.4 to 12.1% by weight, and in a subsequent step b), the partially polymerized mixture which is withdrawn from the reactor in step a) is permitted to further, react until the unreacted alkylene oxide content of the mixture is reduced to 0.001% or less by weight;

wherein the build ratio in step a) is from 4.6 to 16.2 and the overall build ratio is from 4.6 to 16.2, wherein the temperature of the reaction mixture in step b) increases by up to 35° C. as a result of the exothermic polymerization reaction, and wherein the further reaction of the partially polymerized mixture occurs isothermally.

21. The process of claim 20, wherein the resultant polyether polyol has an OH number of from about 112 to about 400.

22. A continuous process for the production of a polyoxyalkylene polyether polyol having an OH number of from 112 to 400 which comprises:

(1) establishing oxyalkylation conditions in a continuous oxyalkylation reactor in the presence of a double metal cyanide catalyst;

(2) continuously introducing alkylene oxide and a low molecular weight starter into said reactor, said starter having a number average molecular weight of from 50 to 250;

and (3) continuously recovering a partially oxyalkylated polyether polyol from the continuous oxyalkylation reactor;

wherein (i) said oxyalkylation in the continuous reactor occurs at a sufficiently high temperature to prevent deactivation of the DMC catalyst; and (4) further reacting the partially oxyalkylated polyether polyol which is recovered from the continuous oxyalkylation reactor thereby forming the polyoxyalkylene polyether polyol having an OH number of from 112 to 400, wherein the further reaction of the partially oxyalkylated polyether polyol occurs isothermally.

23. The process of claim 22, wherein the build ratio in the continuous oxyalkylation reactor is from 4.6 to 16.2 and the overall build ratio is from 4.6 to 16.2, and wherein the reaction temperature of the partially oxyalkylated polyether polyol in step (4) increases by up to 35° C. as a result of the exothermic polymerization reaction.

24. The process of claim 22, wherein said oxyalkylation in the continuous reactor occurs at a temperature of at least 135° C.

25. The process of claim 22, wherein said partially oxyalkylated polyether polyol which is recovered from the continuous oxyalkylation reactor is reacted until the unreacted alkylene oxide content of the mixture is reduced to 0.001% or less by weight.

26. A process for continuously polymerizing an alkylene oxide in the presence of a double metal cyanide (DMC) polymerization catalyst to form a polyether polyol having a hydroxyl content of from about 3.4 to about 9.1% by weight, wherein in a first step a), an initiator compound that has at least two hydroxyl groups per molecule and an equivalent weight of up to 115 and at least one alkylene oxide are fed to a continuous reactor containing a double metal cyanide catalyst, and a partially polymerized mixture is withdrawn from the continuous reactor;

wherein (i) the continuous reactor is maintained at a polymerization temperature that is greater than or equal to 135° C., (ii) the concentration of unreacted alkylene oxide in the contents of the continuous reactor is maintained at a level of from 1 to 3% by weight, and (iii) the hydroxyl content of the reactor contents is maintained at 3.4 to 9.1% by weight, and in a subsequent step b), the partially polymerized mixture which is withdrawn from the reactor in step a) is permitted to further react until the unreacted alkylene oxide content of the mixture is reduced to 0.001% or less by weight;

wherein the build ratio in step a) is from 6.1 to 16.2 and the overall build ratio of from 6.1 to 16.2, wherein the temperature of the reaction mixture in step b) increases by up to about 24° C. as a result of the exothermic polymerization reaction, and wherein the further reaction of the partially polymerized mixture occurs isothermally.

* * * * *